United States Patent

Kershner

[11] Patent Number: 6,093,833
[45] Date of Patent: Jul. 25, 2000

[54] PROCESS FOR PRODUCING TRIVALENT TITANIUM COORDINATION COMPLEX

[75] Inventor: David L. Kershner, Katonah, N.Y.

[73] Assignee: Akzo Nobel N.V., Arnhem, Netherlands

[21] Appl. No.: 09/231,189

[22] Filed: Jan. 14, 1999

[51] Int. Cl.$^7$ .................................................. C07D 307/00
[52] U.S. Cl. ............................................................ 549/210
[58] Field of Search ............................................. 549/210

[56] References Cited

U.S. PATENT DOCUMENTS

| | | | |
|---|---|---|---|
| 4,028,481 | 6/1977 | Shiomura et al. | 526/142 |
| 4,098,907 | 7/1978 | Tokunaga et al. | 526/116 |
| 4,358,572 | 11/1982 | Mack et al. | 526/142 |
| 5,264,590 | 11/1993 | Strickler | 549/208 |
| 5,367,085 | 11/1994 | Strickler | 549/206 |

FOREIGN PATENT DOCUMENTS

| | | | |
|---|---|---|---|
| 000999 | 3/1979 | European Pat. Off. | C08F 10/00 |

OTHER PUBLICATIONS

S.Tyrlik et al., "Reactions of Acetone and Isopropyl Alcohol with the Products of Reduction of Titanium Chlorides with Metallic Magnesium", Journal of Organometallic Chemistry, 93 (1975) 353–362.
Derwent Patent Abstract 05489K/03 (1982).
Derwent Patent Abstract 626188/34 (1979).
Derwent Patent Abstract 47519Y/27 (1977).
Derwent Patent Abstract 90,748P (1967).
Derwent Patent Abstract 59336A/33 (1978).
Derwent Patent Abstract 69365Y/39 (1975).

*Primary Examiner*—Joseph McKane
*Assistant Examiner*—Joseph Murray

[57] ABSTRACT

The disclosure describes a process for preparing a $TiCl_3$ ether complex, such as $TiCl_3(THF)_3$, by reaction of corresponding $TiCl_4$ ether complex with a metal powder, which produces a soluble metal chloride complex, in ether solvent. The $TiCl_3$ ether complex that is prepared has a low aluminum content.

15 Claims, No Drawings

PROCESS FOR PRODUCING TRIVALENT TITANIUM COORDINATION COMPLEX

BACKGROUND OF THE INVENTION

The present invention relates to a process for preparing a Ti (III) coordination complex by the reduction of a Ti (IV) salt, such as a halide (preferably a chloride or bromide) which comprises reducing substantially all of the Ti (IV) salt with a metal powder that forms a soluble metal salt by-product.

The present invention, in a preferred embodiment, describes a process for the preparation of low Al and substantially Al-free $TiCl_3$. Such compounds are useful as polymerization catalyst precursors and as reducing agents in organic synthesis.

Recently it was reported (U.S. Pat. No. 5,264,590) that low-Al stoichiometric $TiCl_3$ (ether) complexes can be prepared by reacting organoaluminum compounds with titanium tetrachloride in certain ethers, such as tetrahydrofuran (THF) to form $TiCl_3$(ether) products. For example, the precipitated $TiCl_3(THF)_3$ product can then be separated from the soluble $AlCl_3(THF)$ complex. However, caution must be exercised in performing such a reaction. Addition of the alkylaluminum reagent to the ether mixture releases heat, so that a low temperature and a slow addition rate are required. Secondly, the alkylaluminum reagent is pyrophoric. Lastly, certain alkyl aluminum compounds may reduce the $TiCl_4$ into the undesirable $TiCl_2$ by-product.

An alternative process for preparing $TiCl_3(THF)_3$ was reported in 1975 (S. Tyrlik et al., J. Organomet. Chem., 1975, 93, 353–362). In this process $TiCl_4$ reacts at room temperature with Al ribbon in THF solvent to form $TiCl_3(THF)_3$:

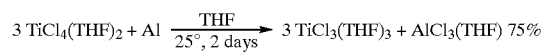

$$3\,TiCl_4(THF)_2 + Al \xrightarrow[25°,\,2\,days]{THF} 3\,TiCl_3(THF)_3 + AlCl_3(THF)\ 75\%$$

This process is convenient for lab-scale preparations, but physically separating the $TiCl_3(THF)_3$ from the Al ribbon may prove to be difficult on large-scale.

SUMMARY OF THE INVENTION

The present invention describes, for example, a process for preparing a $TiCl_3$ ether complex, such as $TiCl_3(THF)_3$, by reaction of corresponding $TiCl_4$ ether complex with a metal powder, which produces a soluble metal chloride complex, in ether solvent.

DESCRIPTION OF THE PREFERRED EMBODIMENTS

The present invention relates generally to the preparation of Ti(III) coordination complexes and specifically to the preparation of Ti(III) coordination complexes by the reduction of Ti(IV) salts using a metal powder, which produces a soluble metal chloride by-product. Ti(III) coordination complexes with ethers are useful intermediates in the formation of Ti(III) metallocene compounds such as dicyclopentadienyl titanium chloride. Such complexes are also useful as agents in certain organic transformation reaction. The metallocene compounds are usually used in combination with activators for stereospecific olefin polymerization.

The Ti(III) coordination complexes can be produced from the hydrogen reduced form of a salt such as $TiCl_3$, but this produces an undesirable HCl product. A process has now been developed which can provide a one-pot synthesis of Ti(III) coordination complexes of low aluminum content starting with inexpensive Ti(IV) salts.

In accordance with this invention there is provided a process for preparing a Ti(III) coordination complex by the reduction of a Ti(IV) salt, said process comprising the steps of (a) forming an ether complex of said Ti(IV) salt by adding a stoichiometric excess of an ether to said salt, and then (b) reducing said complex with a metal powder, which produces a soluble metal chloride complex, in ether solvent.

The anions of the Ti(IV) salts for use as starting materials are not critical and usually have the formula $TiX_4$, where X is halogen. The preferred Ti(IV) compound is $TiCl_4$. Non-limiting examples of ethers for use in forming the coordination complexes include ethylene glycol dimethyl ether (DME), diglyme, triglyme, tetraglyme, tetrahydrofuran (which is preferred), and the like. While the reduction reaction proceeds when such ethers are used, the removal of aluminum trichloride, for example, has been best achieved when THF has been used. Suitable metal powders for use herein as the reducing agent include magnesium, aluminum, and the like.

An inert hydrocarbon solvent can be used when forming the ether complexes of Ti(IV) salts. For example, pentane, isopentane, hexane, cyclohexane, heptane, octane, toluene and the like, may be used. The amount of solvent can range from about 20 to 70 percent by volume of the total volume of reaction mixture. Preferably, the ether is added in a large excess of 10 to 50 equivalents per equivalent of Ti(IV) salt, so as to form a slurry of Ti(IV)-ether complex in an ether and hydrocarbon solvent mixture. The metal powder reducing agent can then be added in about an equivalent amount to the complex (from about 0.8 to about 1.0 equivalent of reducing agent per equivalent of complex). The reaction is very slow at room temperature. Heating the mixture to temperatures of from about 50° C. to 80° C. produces good yields (85–98%) of product in about, for example, 1 to 40 hours. Longer reaction times have been found to be necessary when larger scale equipment has been used. A preferred reaction time is about 24 hours.

One requirement of the metal reducing agents is that they form soluble metal chloride complexes. This allows for efficient separation of the solid $TiCl_3(THF)_3$ from the soluble metal chloride complexes. A second requirement of the invention is that the metal reagent is the limiting reagent in the reaction, so that substantially the entire metal reagent is converted to the metal chloride. Examples of suitable metals are Al and Mg, and they are described in the Examples below. The use of Al is preferred as it produces the desired compound in high yield and in high purity.

The present invention will be further understood by reference to the Examples that follow.

EXAMPLE 1

In this run, $TiCl_4$ (5.8 g, 3.4 ml, 30.5 mmol) was added to 100 ml (70 g) of heptane. The mixture was cooled to 10° C., and THF (20 ml, 18 g, 250 mmol) was added to the heptane solution over a period of about one minute. An exothermic reaction occurred, and a yellow solid formed at once. The mixture was stirred at room temperature for fifteen minutes. The clear colorless supernatant was removed, and 150 ml (130 g) of THF was added to the solid. The mixture was cooled to 10° C., and Mg powder (0.58 g, 24 mmol) was added to the mixture. The temperature of the reaction mixture increased 2° C. during the Mg addition. The mixture was stirred at 10° C. for fifteen minutes. The cooling bath was removed, and the mixture was stirred at room temperature overnight. The mixture was then stirred at reflux for five hours. The resultant brown mixture was allowed to cool to 25° C., and the mixture was filtered. The solid was washed once with 50 ml of THF at 35° C. followed by three 35 ml THF washes at 25° C. The sky-blue solid was dried to yield 10.8 g (29.1 mmol) of $TiCl_3(THF)_3$. The molar yield based on Mg charge was 61%. The solid contained 230 ppm of Mg.

EXAMPLE 2

In this run, $TiCl_4$ (10.4 g, 6.0 ml, 55 mmol) was added to 100 ml (70 g) of heptane. The reactor contents were cooled to 10° C., and THF (20 ml, 18 g, 250 mmol) was added to the heptane solution at room temperature over one minute. An exothermic reaction occurred, and a yellow solid formed at once. The mixture was stirred at room temperature for fifteen minutes. The clear colorless supernatant was removed, and 100 ml (88 g) of THF was added to the solid. The mixture was stirred at room temperature, and Al powder (0.47 g, 17.5 mmol, 99%, from Aldrich, −200 mesh) was added to the reactor in one portion at room temperature. No change in reactor temperature was observed. The yellow mixture was heated to reflux, and it was stirred at reflux for twenty-four hours. The resultant green-blue solution was cooled to room temperature. The mixture was filtered, and the blue solid was washed twice with a 20 ml, 50:50 (vol:vol) $THF:Et_2O$ solution. The solid was dried first under flowing nitrogen followed by vacuum. The yield of $TiCl_3(THF)_3$ was 19.5 g (53 mmol) or 100% based on Al. The Al content of the solid was 0.13 wt %.

EXAMPLE 3

In this run, $TiCl_4$ (10.4 g, 6.0 ml, 55 mmol) was added to 100 ml (70 g) of heptane. The reactor contents were cooled to 10° C., and THF (20 ml, 18 g, 250 mmol) was added to the heptane solution at room temperature over one minute. An exothermic reaction occurred, and a yellow solid formed at once. The mixture was stirred at room temperature for fifteen minutes. The clear colorless supernatant was removed, and 150 ml (133 g) of THF was added to the solid. The mixture was stirred at room temperature, and Al powder (0.471 g, 17.5 mmol, 99%, from Aldrich, −200 mesh) was added to the reactor in one portion. No change in reactor temperature was observed. The yellow mixture was heated to reflux, and it was stirred at reflux for twenty-four hours. The resultant green-blue solution was cooled to room temperature. The mixture was filtered, and the blue solid was washed three times with a 20 ml, 50:50 (vol:vol) $THF:Et_2O$ solution. The solid was dried first under flowing nitrogen followed by vacuum. The yield of $TiCl_3(THF)_3$ was 16.5 g (44.6 mmol) or 85% based on Al. The Al content of the solid was 0.073 wt %.

EXAMPLE 4

A $TiCl_3(THF)_3$ solid was prepared from 0.460 g (17.0 mmol) of Al powder in the same manner as described in Example 3. The only difference was that the product was washed twice with 30 ml of a 2:1 (vol:vol) THF:heptane solution. The yield of product was 17.25 g (46.6 mmol) or 92% based on Al. The Al content of the solid was 0.033 wt %.

EXAMPLE 5

In this run, $TiCl_3(THF)_3$ was prepared by adding THF (100 ml) to a solution of heptane (50 ml) and $TiCl_4$ (6.0 ml). This reaction mixture was not filtered prior to addition of Al powder (0.446 g, 16.5 mmol). After twenty hours of reflux, the resultant blue solid was filtered and washed with a THF:heptane (2:1 vol:vol) solvent system as described in Example 4. The yield of product was 15.06 g (40.7 mmol) or 82% based on Al.

EXAMPLE 6

In this run, $TiCl_3(THF)_3$ was prepared in a similar manner to that of Example 5 except the $TiCl_4(THF)_2$ intermediate was prepared by adding 100 ml of THF to a solution of $TiCl_4$ (6.0 ml) in 25 ml of heptane. The yield of product was 17.43 g or 91% based on Al charge of 0.464 g (17.2 mmol). The Al content of the solid was 360 ppm.

EXAMPLE 7

In this run, $TiCl_3(THF)_3$ was prepared in a similar manner to that of Example 5 except no heptane was used to prepare the $TiCl_4(THF)_2$ intermediate. Neat $TiCl_4$ (6.0 ml) was added to THF (100 ml) at 3° C. over ten minutes. The reactor was held in an ice batch during the addition, and the reactor contents reached 13° C. at the end of the addition. The yield of product was 16.75 g or 85% based on Al charge of 0.478 g (17.7 mmol). The Al content of the solid was 840 ppm.

EXAMPLE 8

In this run, $TiCl_3(THF)_3$ was prepared in a similar manner to that of Example 5 except the $TiCl_4(THF)_2$ intermediate was prepared by adding a solution of $TiCl_4$ (6.0 ml) in heptane (25 ml) to 100 ml of THF. The yield of product was 16.75 g or 92% based on Al charge of 0.460 g (17.0 mmol). The Al content of the solid was 265 ppm.

The foregoing Examples are being provided to illustrate certain embodiments of the present invention and, for that reason, should not be construed in a limiting fashion. The scope of protection sought is set forth in the claims that follow.

I claim:

1. A process for preparing a Ti (III) coordination complex by the reduction of a Ti (IV) salt which comprises reducing substantially all of the Ti (IV) salt with a metal powder that forms a soluble metal salt by-product.

2. A process as claimed in claim 1 wherein the Ti (IV) salt is in the form of an ether complex.

3. A process as claimed in claim 1 wherein the Ti (IV) salt is titanium tetrachloride.

4. A process as claimed in claim 1 wherein the Ti (IV) salt is in the form of an ether complex and the Ti (IV) salt is titanium tetrachloride.

5. A process as claimed in claim 1 wherein the Ti (IV) salt is in the form of a tetrahydrofuran complex and the Ti (IV) salt is titanium tetrachloride.

6. A process as claimed in claim 1 wherein the metal is magnesium.

7. A process as claimed in claim 1 wherein the metal is aluminum.

8. A process as claimed in claim 6 wherein the Ti (IV) salt is in the form of an ether complex.

9. A process as claimed in claim 6 wherein the Ti (IV) salt is titanium tetrachloride.

10. A process as claimed in claim 6 wherein the Ti (IV) salt is in the form of an ether complex and the Ti (IV) salt is titanium tetrachloride.

11. A process as claimed in claim 6 wherein the Ti (IV) salt is in the form of a tetrahydrofuran complex and the Ti (IV) salt is titanium tetrachloride.

12. A process as claimed in claim 7 wherein the Ti (IV) salt is in the form of an ether complex.

13. A process as claimed in claim 7 wherein the Ti (IV) salt is titanium tetrachloride.

14. A process as claimed in claim 7 wherein the Ti (IV) salt is in the form of an ether complex and the Ti (IV) salt is titanium tetrachloride.

15. A process as claimed in claim 7 wherein the Ti (IV) salt is in the form of a tetrahydrofuran complex and the Ti (IV) salt is titanium tetrachloride.

* * * * *